US006708064B2

(12) United States Patent
Rezai

(10) Patent No.: US 6,708,064 B2
(45) Date of Patent: Mar. 16, 2004

(54) MODULATION OF THE BRAIN TO AFFECT PSYCHIATRIC DISORDERS

(76) Inventor: Ali R. Rezai, 28 Haskell Dr., Bratenahl, OH (US) 44108

(*) Notice: Subject to any disclaimer, the term of this patent is extended or adjusted under 35 U.S.C. 154(b) by 0 days.

(21) Appl. No.: 10/036,340

(22) Filed: Dec. 24, 2001

(65) Prior Publication Data

US 2002/0151939 A1 Oct. 17, 2002

Related U.S. Application Data

(63) Continuation-in-part of application No. 09/574,495, filed on May 19, 2000, now abandoned, and a continuation-in-part of application No. 09/574,293, filed on May 19, 2000, now abandoned, and a continuation-in-part of application No. 09/575,292, filed on May 19, 2000, now abandoned, and a continuation-in-part of application No. 09/511,845, filed on Feb. 24, 2000, and a continuation-in-part of application No. 09/511,844, filed on Feb. 24, 2000, now abandoned, and a continuation-in-part of application No. 09/511,843, filed on Feb. 24, 2000, now Pat. No. 6,418,344, and a continuation-in-part of application No. 09/511,842, filed on Feb. 24, 2000, now abandoned.

(51) Int. Cl.$^7$ ................................. A61N 1/18
(52) U.S. Cl. ..................... 607/45; 607/2; 607/3
(58) Field of Search .................. 607/45, 2, 3

(56) References Cited

U.S. PATENT DOCUMENTS

| 5,938,688 | A | * | 8/1999 | Schiff | 607/45 |
|---|---|---|---|---|---|
| 6,066,163 | A | * | 5/2000 | John | 607/45 |
| 6,167,311 | A | * | 12/2000 | Rezai | 607/45 |
| 6,463,328 | B1 | * | 10/2002 | John | 607/45 |
| 6,539,263 | B1 | * | 3/2003 | Schiff et al. | 607/45 |

* cited by examiner

*Primary Examiner*—Carl Layno
(74) *Attorney, Agent, or Firm*—Raymond A. Miller; Pepper Hamilton LLP

(57) ABSTRACT

A method for treating neurological conditions by proper placement of a probe and sensing, stimulating or both areas of the brain especially the intralaminar nuclei (ILN"). Moreover, stimulation is controlled and offered when certain conditions within the area of interest are detected. Stimulation and sensing include electrical, chemical or combinations thereof.

23 Claims, 6 Drawing Sheets

Figure 5

| Location | | Lateral X | AP Y | Sagittal Z |
|---|---|---|---|---|
| | | (all measurements are in mm and relative to AC-PC line) | | |
| Cortical and Limbic | | | | |
| Pre-frontal cortex | PFC | Falx to Sphenoid ridge | 20 mm ant. to coronal suture and anteriorly | Superior, middle and inferior frontal gyrus |
| Orbitofrontal cortex | OFC | Medial to inferior frontal gyrus and lateral to gyrus rectus | Anterior commissure and anteriorly | Frontal fossa base to cingulate sulcus |
| Anterior limb of the internal capsule | IC-ant | 10 to 20 | AC: 3 to 10 | 10 to 0 |
| Cingulate cortex | Cing | 5 to 9 | 15 to 25 posterior to frontal horn tip | 1 to 5 above ventricular roof |
| Amygdala | Amy | 12 to 22 | MCP: 3 to 15 | -15 to -25 |
| Hippocampus | Hipp | medial to temporal horn | amygdala to 30 posterior | -10 to -25 |
| Mamillary Bodies | MB | 0 to 5 | MCP: 2 to 12 | -5 to -15 |
| Lateral Hypothlamus | LH | 5 to 15 | AC: 5 to -5 | 0 to -10 |
| Basal Ganglia | | | | |
| Nucleus Accumbens | nAcc | 5 to 13 | AC: 0 to 5 | 3 to -5 |
| Caudate nucleus | Caud | 12 to 25 | AC: 0 to 10 | 0 to 15 |
| Ventral Striatum | VS | 15 to 30 | MCP: 0 to 10 | 3 to 10 |
| Ventral Pallidum | VP | 15 to 30 | MCP: 0 to 6 | 3 to 10 |
| Thalamus | | | | |
| Anterior nucleus of the thalamus | Ant | 2 to 12 | AC: 7 to -5 | 0 to 13 |
| Dorsomedial nucleus of the thalamus | DM | 0 to 10 | AC: 0 to -5 | 0 to 13 |
| Brainstem | | | | |
| Locus Ceruleus | LC | 0 to 7 | MCP: -10 to -20 | -5 to -20 |
| Dorsal Raphe Nucleus | DR | 0 to 7 | MCP: -10 to -20 | -3 to -15 |
| Ventral Tegmentum | VT | 0 to 15 | MCP: 3 to -10 | -5 to -15 |
| Substantia Nigra Pars Compacta | SNc | 5 to 12 | MCP: 5 to -12 | -5 to -20 |
| Substantia Nigra Pars Reticulata | SNr | 6 to 15 | MCP: 5 to -12 | -5 to -20 |
| Superior Colliculus | SC | 0 to 12 | PC: -5 to -15 | 0 to -7 |

Additional details of the correlation of areas of the brain to the intralaminar nuclei subdivisions and their projections can be found in Jones, et al. Eds., The Thalamus Amesterdam: Elsevier (1995), which is hereby incorporated by reference in its entirety.

MCP: Relative to Midcommisural point (anterior is positive)
AC: Relative to the anterior commisure (anterior is positive)
PC: Relative to the posterior commisure (anterior is positive)
Sagittal: Superior is positiv , Inferior is negative

Figure 6

| Location | Abbrev | Lateral X | AP Y | Sagittal Z | Interconnections |
|---|---|---|---|---|---|
| | | (all measurements are in mm relative to AC-PC Line) | | | |
| Intralaminar thalamic nuclei | ILN | | | | |
| Anterior ILN | | 7 to 13 | MCP to 10 anterior | 0 to 13 | |
| · Central Lateral (CL) | ILN-CL | | | | Prefrontal cortex, parietal cortex, visual association cortex, motor cortex |
| Paracentralis (Pc) | ILC-Pc | | | | Prefrontal cortex, orbitofrontal cortex, anterior cingulate |
| Paralamellar MD | ILC-Pl | | | | Prefrontal Cortex, temporal association cortex, anterior parietal |
| Posterior ILN | | 5 to 10 | MCP: -5 to PC: -7 | 0 to 13 | |
| Centromedian(Cm) | ILN-CM | | | | Prefrontal cortex, premotor cortex, parietal association cortex |
| Parafasicularis(Pf) | ILN-Pf | | | | Prefrontal cortex, premotor cortex, parietal association cortex |
| Midline ILN | | 2 to 8 | MCP to 10 anterior | 0 to 13 | |
| Paraventricularis (Pv) | ILN-Pv | | | | Amygdala, Limbic System, hippocampus |
| Central Medial (CM) | | | | | Orbitofrontal, limbic System, Hippocampus, Amygdala |
| Midline Nuclei | ILN-mid | | | | |

MCP  Mid commisural point (anterior is positive)
AC   Anterior commisure
PC   Posterior commisure
Sagittal  Superior is positive, Inferior is negative

MODULATION OF THE BRAIN TO AFFECT PSYCHIATRIC DISORDERS

CROSS-REFERENCE TO RELATED APPLICATIONS

This application is a continuation-in-part of each of U.S. application Ser. Nos. 09/511,842 now abandoned; 09/511,843 now U.S. Pat. No. 6,418,344; 09/511,844 now abandoned; 09/511,845; all filed Feb. 24, 2000; and U.S. application Ser. Nos. 09/575,292 now abandoned; 09/575,293 now abandoned; 09/574,495 now abandoned all filed May 19, 2000.

BACKGROUND OF THE INVENTION

The treatment of psychiatric disorders by surgical means has an extensive history. In the early 1930's, Fulton and Jacobsen first recognized that experimentally induced neurotic behavior in chimpanzees could be abolished by frontal lobectomy. Within a few years, Freeman and Watts developed the first psychosurgical procedure for humans known as the frontal lobotomy.

As the inherent physiology of the frontal lobe became more evident, the original freehand procedure of Freeman and Watts became less and less extensive. By the late 1940's, the method of stereotaxis, in which the patient's brain is modeled in 3-dimensional space for exquisite targeting accuracy, merged with lesioning techniques resulting in an even more efficacious and safe psychosurgical procedure. Further developments of stereotactic equipment have combined with novel advancements in functional and anatomic imaging as well as intraoperative electrophysiological mapping to encompass the state of the art in the neurosurgical treatment of neurological and psychiatric disorders today.

While technologically improved and more precise, today's surgical lesioning techniques have the fundamental limitation of being inherently irreversible and are essentially a "one shot" procedure with little chance of alleviating or preventing potential side effects. In addition, there is a limited possibility to provide continuous benefits as the disease progresses and the patient's symptoms evolve.

Within the field of neurosurgery, the use of electrical stimulation for treating neurological disease, including such disorders as movement disorders including Parkinson's disease, essential tremor, dystonia, and chronic pain, has been widely discussed in the literature. It has been recognized that electrical stimulation holds significant advantages over lesioning, inasmuch as lesioning can only destroy nervous system tissue. In many instances, the preferred effect is to stimulate to increase, decrease, or block neuronal activity. Electrical stimulation permits such modulation of the target neural structures and, equally importantly, does not require the destruction of nervous tissue. In many ways, this is analogous to a reversible and adjustable lesioning procedure.

To date, however, disorders manifesting gross physical dysfunction, not otherwise determinable as having psychiatric and/or behavioral origins, comprise the vast majority of those pathologies treated by deep brain stimulation. A noteworthy example of treatment of a gross physical disorder by electrical stimulation is included in the work of Alim Benabid, who developed a method of reducing the tremor associated with Parkinson's disease by the application of a high frequency electrical pulse directly to the thalamus. This has also been applied in the subthalamic nucleus for the treatment of Parkinson's rigidity, slowness of movement, walking and other movement (see e.g. the New England Journal of Medicine, Vol. 339, October 1998, pp. 105–1111, Electrical Stimulation of the Subthalamic Nucleus in Advanced Parkinson's Disease).

Efforts have been made to treat psychiatric disorders with peripheral/cranial nerve stimulation. A recent investigational protocol has demonstrated partial benefits with vagus nerve stimulation in patients with depression (Biological Psychiatry 47: 216–286, 2000) Additional clinical trials with depression and vagus nerve stimulation are underway. Another noteworthy example is the effort to control depression and compulsive eating disorders by stimulation of the vagus nerve is provided in U.S. Pat. No. 5,263,480. This treatment seeks to induce a satiety effect by stimulating the afferent vagal fibers of the stomach. For patients having weak emotional and/or psychological components to their eating disorders, this treatment can be effective insofar as it eliminates the additional (quasi-normal) physio-chemical stimulus to continue eating. This is especially true for patients who exhibit subnormal independent functioning of these fibers of the vagus nerve. For compulsive eating patients who are not suffering from an insufficient level of afferent vagal nerve activity resulting from sufficient food intake, however, the over stimulation of the vagus nerve and potential resultant over abundance of satiety mediating chemicals (cholecystokinin and pancreatic glucagon) may have little effect. It has even been suggested that continued compulsive eating, despite overstimulation of the vagus nerve, may exacerbate the emotional component of the patient's disorder. This, therefore, begs the question, is vagus nerve stimulation useful in treating the psychological component of the disorder of compulsive eating, or is it simply a method of minimizing the additional, but natural, pressures to eat because of normal physical hunger. More generally, the question may be asked, is peripheral nerve stimulation of any kind the most appropriate method of treatment for disorders that are, at the core, the result of a pathology exhibited in the brain. The effect of this peripheral stimulation seems to be non-specific and a secondary phenomenon. Indeed functional brain imaging studies have demonstrated induction of intracranial thalamic activity thus providing evidence for an indirect action of the peripheral stimulators. A more appropriate target may be the brain region which is functioning abnormally.

SUMMARY OF THE INVENTION

Surgical treatments for psychiatric disorders that have traditionally been treated by behavioral therapy or psychiatric drugs, have been largely limited to the stereotactic lesioning such as cingulotomy, capsulotomy, subcaudate tractotomy, and limbic leucotomy. Such procedures have been applied to date in the treatment of affective disorders and anxiety disorders. If one critically examines the results of these procedures in the literature, it becomes apparent, when applied to a carefully selected patient population in conjunction with modern stereotactic surgical equipment and imaging techniques, that these procedures are both efficacious and safe. In fact, in a certain subset of patients who have failed all conventional treatments, these neurosurgical procedures may be the only treatment options available. Therefore, electrical and/or chemical neurosurgical neuromodulating techniques, with their inherent reversibility and adjustability, offer a safer and potentially more effective alternative to lesioning procedures. The present invention relates to modulation of neuronal activity to affect psychological or psychiatric activity. The present invention finds particular application in the modulation of neuronal function or processing to affect a functional outcome. The modulation of nueronal function is particularly useful with regard to the prevention, treatment, or modulation of psychiatric, psychological, behavioral, mood, and thought activity. (unless otherwise indicated these will be collectively referred to herein as "psychological activity" or "psychiatric activity"). When referring to a pathological or undesirable condition associated with the activity, reference may be made to "psychiatric disorder" or "psychological disorder" instead of psychiatric or psychological activity. Although the activity to be modulated usually manifests itself in the form of a disorder such as addiction/substance abuse, obsessive compulsive disorder, generalized anxiety disorder, post traumatic stress disorder, panic attacks, social phobia, major depression, bipolar disorder, schizophrenia, it is to be appreciated that the invention may also find application in conjunction with enhancing or diminishing any neurological or psychiatric function, not just abnormality or disorder. Psychiatric activity that may be modulated can include, but not be limited to, normal functions such as fear, anger, anxiety, euphoria, sadness, and the fight or flight response.

The present invention finds particular utility in its application to human psychological or psychiatric activity/disorder. However, it is also to be appreciated that the present invention is applicable to other animals which exhibit behavior that is modulated by the brain. This may include, for example, primates, canines, felines, elephants, dolphins, etc. Utilizing the various embodiments of the present invention, one skilled in the art may be able to modulate the functional outcome of the brain to achieve a desirable result.

One technique that offers the ability to affect neuronal function in a reversible and dynamic fashion is the delivery of electrical stimulation for neuromodulation directly to target tissues via an implanted electrode assembly.

Another technique that offers the ability to affect neuronal function in a reversible and dynamic fashion is the delivery of drugs or neuromodulating chemicals directly to target tissues via a subcutaneously implanted pump and/or a slow release matrix Such drugs, either traditional psychiatric agents or chemicals mimicking neurotransmitters, could be instilled precisely at such low doses as to completely avoid the side effects so common to modern pharmacotherapy and to provide a physiological neuromodulation. Such doses could also be tailored in magnitude with respect to a particular patient's varying symptomatology. A chemical neuromodulating system may also be implanted as a primary treatment strategy or in combination with an electrically based one.

A combination therapeutic approach, one combining electrical and chemical means, would be penultimate to generating healthy neuronal tissue itself. In addition to the stimulation and chemical modulation, the implantable device could also have chemical and/or electrical sensing functions that can be coupled to the chemical and electrical output of the modulating device.

Initially there is an impetus to treat psychiatric disorders with direct modulation of activity in that portion of the brain causing the pathological behavior. In this regard there have been a large number of anatomical studies that have helped to identify the neural structures and their precise connections which are implicated in psychiatric activity/disorders. These are the structures that are functioning abnormally and manifesting in psychiatric/behavioral/addiction disorders. Numerous anatomical studies from autopsies, animal studies, and imaging such as computerized tomography (CT) scans, and magnetic resonance imaging (MRI) scans have demonstrated the role of these structures and their connections in psychiatric activity/disorders. In addition to these anatomical studies, a number of physiological techniques and diagnostic tools are used to determine the physiological aberrations underlying these disorders. This includes electrical methods such as electroencephalography (EEG), magnetoencephalography (MEG), as well as metabolic and blood flow studies such as functional magnetic resonance imaging (fMRI), and positron emission tomography (PET). The combination of the anatomical and physiological studies have provided increased insight into our understanding of the structures which are involved in the normal functioning or activity of the brain and the abnormal functioning manifesting in psychiatric, behavioral and addiction disorders.

The primary areas of interest for psychiatric acitivty/disorders include the pre-frontal cortex, orbitofrontal cortex, anterior limb of the internal capsule, Nucleus Accumbens, ventral striatum, the ventral Pallidum anterior nucleus of the thalamus, dorsomedial nucleus of the thalamus, intralaminar thalamic nuclei, the cingulate cortex, Amygdala, Hippocampus, Mamillary bodies, the lateral hypothlamus the Locus Ceruleus, the Dorsal Raphe Nucleus, ventral tegmentum, the Substantia Nigra Pars Compacta and reticulata. These structures are schematically shown in FIGS. 1 and 2 and are implicated in psychiatric activity and disorders.

One embodiment of the present invention relates generally to modulating the pathological electrical and chemical activity of the brain by electrical stimulation and/or direct placement of neuromodulating chemicals within the corresponding areas of abnormal function and activity. In accordance with this embodiment of the present invention, a method is provided which provides surgical treatment of psychiatric disorders (e.g. addictions/substance abuse, obsessive compulsive disorder, generalized anxiety disorder, post traumatic stress disorder, panic attacks, social phobia, major depression, bipolar disorder, schizophrenia, and addictions) by implantation of stimulating electrodes and/or drug/chemical delivery micro infusion at the locations detailed herein.

In another aspect, the present invention also provides methods for identifying the proper positioning of the electrodes and/or chemical/drug delivery catheters and microinfusion systems within the intralaminar nucleus in the thalamus to affect their associated connections in the thalamus and other subcortical and cortical areas such as the pre-frontal cortex, orbitofrontal cortex, anterior limb of the internal capsule, Nucleus Accumbens, ventral striatum, the ventral Pallidum, anterior nucleus of the thalamus, dorsomedial nucleus of the thalamus, intralaminar thalamic nuclei, the cingulate cortex, Amygdala, Hippocampus, Mamillary bodies, the lateral hypothlamus the Locus Ceruleus, the Dorsal Raphe Nucleus, ventral tegmentum, the Substantia Nigra Pars Compacta, and reticulata In one embodiment of the invention, therefore, the proximal end of the electrode and/or catheter is coupled to an electrical signal source and/or drug delivery pump which, in turn, is operated to stimulate the predetermined treatment site in regions described above such that the functional outcome is achieve or the clinical effects of the psychiatric and disorders are reduced.

In an another embodiment of the present invention, a method of determining the proper therapeutic treatment (i.e., the proper position or placement of the electrodes and/or catheters) for a specific psychiatric, behavioral, addictive disorder comprising the steps of: identifying a large sampling of patients (each exhibiting a common specific psychiatric/addictive disorder or activity) and then identifying which common region of the brain exhibits pathological electrical and/or chemical activity during manifestations of the specific psychiatric disorder. The common regions demonstrating this pathological activity constitute the predetermined treatment site, wherefore a suitable means for affecting the activity of said predetermined treatment site may be employed to ameliorate/improve the psychiatric disorder/activity generically with a high probability of success.

In particular, the common regions identified above, are herein identified by their known anatomical connections and physiological functioning as being actively involved in channeling or generating the pathological electrical activity associated with psychiatric activity/disorders. It is important to note that these regions, including their functions and connections, are a common structural feature of human brains, and therefore is a common target across a large number of patients. As suggested above, this commonality of function and structure in these structures implicated in the psychiatric activity or disorder allows for common treatment targeting, even in instances wherein different patients have other disparate locations within their brains that also exhibit pathological electrical and/or metabolic activity.

In yet another embodiment of the present invention a method of treating a a specific psychiatric disorder is provided which is comprised of identifying the region of the ILN associated/interconnected with the areas (e.g. prefrontal cortex or basal ganglia) manifesting the pathological electrical activity relating to the specific psychiatric disorder. These connections are demonstrated more fully in the detailed description below and the accompanying Figures. The common regions demonstrating this pathological activity constitute the predetermined treatment site, wherefore a suitable means for affecting the activity of said predetermined treatment site may be employed to ameliorate the psychiatric activity/disorder.

In yet another embodiment of the present invention, a method of treating an addiction associated with an area of interest in a brain comprising: implanting a probe in the area of interest, the probe including a chemical sensor and a chemical dispenser; coupling an end of the probe in fluid communication with the chemical dispenser to a chemical pump; and sensing in the area of interest a determined chemical condition; and operating the pump to urge a chemical through the chemical dispenser into the area of interest to thereby treat the addiction. The step of sensing may occur at a location distal from the device location, may occur at a distant site in the brain epidurally, subdurally, or from the scalp, or may be at the local milieu of the electrode and/or microinfusion cannula.

In yet another embodiment of the present invention, a method of treating an addiction associated with an area of interest in a brain comprising: implanting an electrode in the area of interest of a brain so that a distal end lies in communication with a predetermined site in the area of interest; coupling a proximal end of the electrode to at least one remotely located device; sensing electrical activity in the area of interest; and operating the electrode to provide electrical stimulation to the area of interest in response to the electrical activity to thereby treat the addiction.

In yet another embodiment of the present invention, a method of treating an addiction associated with an area of interest in a brain comprising: implanting an electrode in an intralaminar nucleus of a brain so that a distal end lies in communication with a predetermined site in the intralaminar nucleus; coupling a proximal end of the electrode to at least one remotely located device; sensing electrical activity in the area of interest; and operating the electrode to provide electrical stimulation to the intralaminar nucleus in response to the electrical activity to thereby treat the addiction.

In yet another embodiment of the present invention, a method of determining a treatment for, and subsequently treating a specific disorder comprising: identifying a set of patients, where the patients each exhibit a common specific disorder; placing a probe relative to a brain of at least one patient from the set of patients so that an end of the probe lies in communication with a treatment site in the brain; and operably connecting a second end of the probe to a remote device, where the remote device detects a specified condition in the treatment site and applies a corrective action based on the detected condition. The corrective action may increase thalamic activity or may decrease activity in the dorsomedial thalamus. The disorder may be selected from the group consisting of anxiety disorder, affective disorder, and substance abuse disorder.

In yet another embodiment of the present invention, a method of treating a disorder associated with a specific area in a brain comprising: implanting a device in contact with an intralaminar nuclei of the brain; sensing activity in a specific area of the brain; and operating the device to modulate the intralaminar nuclei in response to said activity to thereby affect the disorder associated with the specific area of the brain. The stimulation may be electrical, chemical or a combination thereof. The stimulation may be continuously, intermittently, or periodically. The specific area of the brain may be different than the intralaminar nuclei. The step of sensing may occur at a location distal from the device location, may occur at a distant site in the brain epidurally, subdurally, or from the scalp, or may be at the local milieu of the electrode and/or microinfusion cannula. The specific area may be selected from the group consisting of the pre-frontal cortex, orbitofrontal cortex, anterior limb of the internal capsule, Nucleus Accumbens, ventral striatum, the ventral Pallidum anterior nucleus of the thalamus, dorsomedial nucleus of the thalamus, intralaminar thalamic nuclei, the cingulate cortex, Amygdala, Hippocampus, Mamillary bodies, the lateral hypothlamus the Locus Ceruleus, the Dorsal Raphe Nucleus, ventral tegmentum, the Substantia Nigra Pars Compacta and reticulata. The psychiatric disorders may be selected from the group consisting of obsessive compulsive disorder, generalized anxiety disorder, post traumatic stress disorder, panic attacks, social phobia, major depression, bipolar disorder, schizophrenia, and substance abuse disorders/addictions.

In yet another embodiment of the present invention, a method of affecting a specific area in a brain comprising: placing an electrode in contact with an intralaminar nuclei of the brain; and operating the device to provide stimulation to the intralaminar nuclei to thereby affect the specific area of the brain. The stimulation may be electrical, chemical or a combination thereof. The stimulation may be continuously, intermittently, or periodically. The specific area of the brain may be different than the intralaminar nuclei. The step of sensing may occur at a location distal from the device location, may occur at a distant site in the brain epidurally, subdurally, or from the scalp, or may be at the local milieu of the electrode and/or microinfusion cannula. The specific area may be selected from the group consisting of the pre-frontal cortex, orbitofrontal cortex, anterior limb of the internal capsule, Nucleus Accumbens, ventral striatum, the ventral Pallidum anterior nucleus of the thalamus, dorsomedial nucleus of the thalamus, intralaminar thalamic nuclei, the cingulate cortex, Amygdala, Hippocampus, Mamillary bodies, the lateral hypothlamus the Locus Ceruleus, the Dorsal Raphe Nucleus, ventral tegmentum, the Substantia Nigra Pars Compacta and reticulate. The psychiatric disorders may be selected from the group consisting of obsessive compulsive disorder, generalized anxiety disorder, post traumatic stress disorder, panic attacks, social phobia, major depression, bipolar disorder, schizophrenia, and substance abuse disorders/addictions.

In yet another embodiment of the present invention, a method of effecting psychiatric activity in a patient comprising: identifying a portion of the patient's ILN which is in communication with a predetermined region of the patient's brain, said predetermined region of said patient's brain being associated with the psychiatric activity; and modulating the portion of the patient's ILN to effectuate the psychiatric activity. The identification of a portion of the patient's ILN may already be identified. The identifying step may be independent of an exhibition of a pathologic condition in the predetermined region of said patient's brain. The psychiatric activity may be selected from the group consisting of happiness, fear, anger, anxiety, euphoria, and sadness. The modulation of the portion of the patient's ILN is accomplished using chemical stimulation, electrical stimulation, or combinations thereof.

Still further aspects of the present invention will become apparent to those of ordinary skill in the art upon reading and understanding the following detailed description of the preferred embodiments.

BRIEF DESCRIPTION OF THE DRAWINGS

The invention may take form in various components and arrangements of components and in various steps and arrangements of steps. The drawings are only for purposes of illustrating the preferred embodiments and are not to be construed as limiting the invention.

FIG. 5 is a table providing coordinates of various regions of the brain; and

FIG. 6 is a table providing coordinates of various regions of the ILN.

DETAILED DESCRIPTION OF THE PREFERRED EMBODIMENTS

Figure 1:
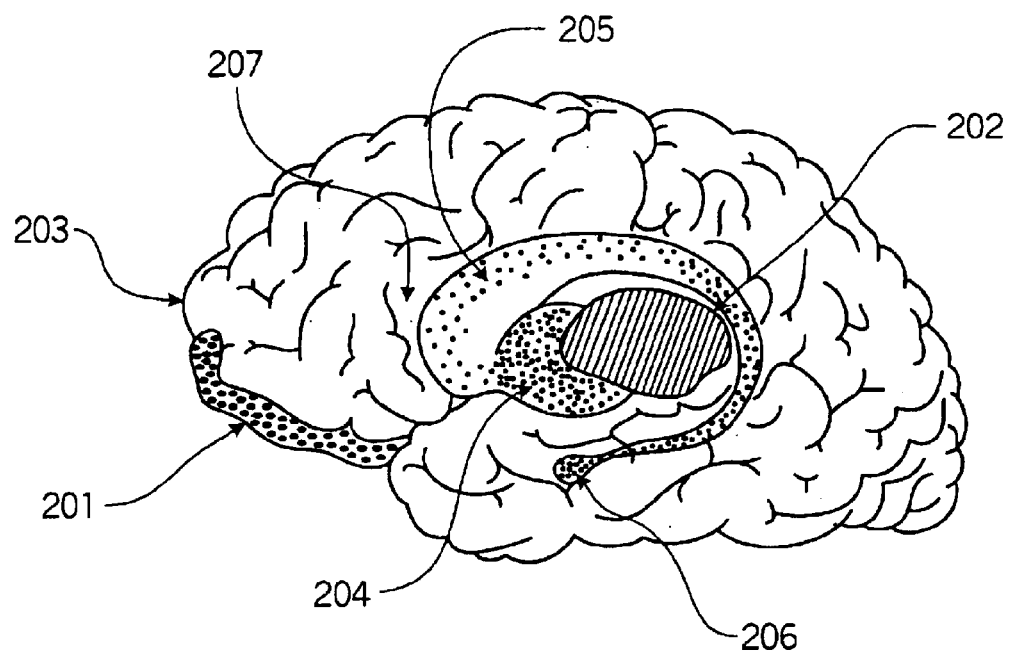
FIG. 1 is a side view of the brain with an implanted electrical/chemical delivery and sensing device illustrating components of the brain involved in psychiatric activity and disorders.

While the present invention will be described more fully hereinafter with reference to the accompanying drawings, in which particular embodiments are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

U.S. Pat. No. 6,167,311 to Rezai, U.S. Pat. No. 5,938,688 to Schiff, and U.S. Pat. Nos.: 5,782,798; 5,975,085; 6,128,537; and 6,263,237 to Rise are all incorporated herein in their entirety by reference thereto.

One aspect of the present invention comprises a method of identifying patients with psychiatric disorders. This process begins with the accumulation of physical, chemical, and historical behavioral data on each patient. A collection of patients who have been identified as exhibiting similar clinical symptoms are then grouped together and subject to a series of common non-invasive brain imaging studies.

One important aspect of the present invention is the recognition that it is desirable to affect psychiatric activity and disorders with modulation of activity in that portion of the brain causing the abnormality or in the related circuitry. Anatomical studies from animals, autopsies as well as MRI and CT imaging have been correlated to determine the structures and their connections which are implicated in psychiatric disorders.

A variety of techniques can be used to determine normal and abnormal brain function that can result in disorders. Functional brain imaging allows for localization of specific normal and abnormal functioning of the nervous system. This includes electrical methods such as electroencephalography (EEG), magnetoencephalography (MEG), as well as metabolic and blood flow studies such as functional magnetic resonance imaging (fMRI), and positron emission tomography (PET) which can be utilized to localize brain function and dysfunction. The complimentary features of these techniques allows one to routinely and reproducibly localize and detect brain function and dysfunction to be localized.

The use of magnetoencephalography (MEG scans) has permitted quantification of electrical activity in specific regions of the brain. It has been proposed that MEG scans may be used to identify regions exhibiting pathological electrical activity. However, simply identifying the regions of the brain which are exhibiting pathological electrical activity for a specific patient may not be sufficient to generalize across a large population of patients, even if they are exhibiting identical disorders. The correlation of specific areas of the brain that are not demonstrating normal activity across a group of patients exhibiting similar clinical symptoms and who are similarly diagnosed should not be assumed a priori.

FIG. 1 illustrates a side view of a human brain having a stimulation electrode implanted in a pre-determined region of the brain (e.g. the thalamus) in accordance with one aspect of the present invention. This Fig. demonstrates the major overall structures implicated in the psychiatric activity and disorders. This includes the orbitofrontal cortex (201), thalamus (202), prefrontal cortex (203), putamen and globus pallidus (204), caudate (205), amygdala (206) and cingulate cortex (207). These structures are interlinked via precise circuits. For example, the thalamus has over 100 subsections, some of which are implicated in psychiatric disorders (see below). The details of how these structures interplay are described below.

Figure 2:
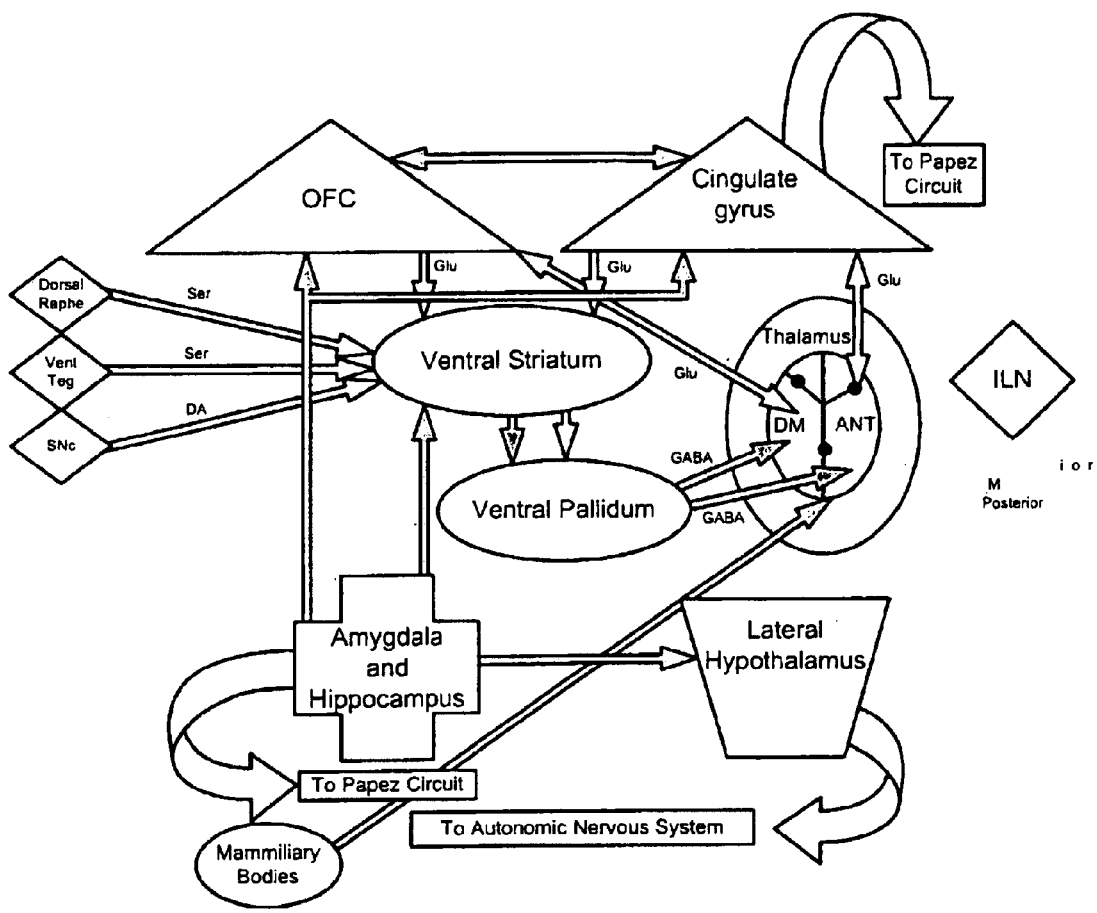
FIG. 2 schematically illustrates the various structures of the brain and their inter-connections involved with the neural circuitry of psychiatric activity/disorders.

The structures and their connections/projections, which are implicated in the circuitry of psychiatric activity and disorders, are shown in FIG. 2. As shown in the in FIG. 5 these structures and their X (Medial-lateral), Y (anterior-posterior) and Z (superior-inferior) stereotactic coordinates with respect to the anterior commissure (AC) and the posterior commissure (PC) are identified.

Much of the teaching below will focus on the specific placement of the neuromodulation device within the various neuronal structures and their connections which are implicated in psychiatric disorders (psychological, behavioral, addictive/substance abuse and developmental disorders including obsessive compulsive disorder, generalized anxiety disorder, post traumatic stress disorder, panic attacks, social phobia, major depression, bipolar disorder, schizophrenia, addictions autism, dyslexia). These structures include the pre-frontal cortex, orbitofrontal cortex, anterior limb of the internal capsule, Nucleus Accumbens, ventral striatum, the ventral Pallidum anterior nucleus of the thalamus, dorsomedial nucleus of the thalamus, intralaminar thalamic nuclei, the cingulate cortex, Amygdala, Hippocampus, Mamillary bodies, the lateral hypothlamus the Locus Ceruleus, the Dorsal Raphe Nucleus, ventral tegmentum, the Substantia Nigra Pars Compacta and reticulata . Those of ordinary skill in the art understand that the teachings here are broadly applicable to treating disorders anywhere in the brain.

Once a patient has been identified as exhibiting abnormal clinical behavior symptomatic of one of these disorders, subsequent pre-operative brain imaging scans are used to support the presumption that the abnormal signals associated with the disorder are being channeled through one of these related regions and then surgical intervention with electrical and/or chemical stimulation is taken.

Different aspects of the present invention comprise new and novel methods of treating disorders by implantation of probes into specific area of the brain. It is to be understood that the term probes, as used here, is meant to include stimulation electrodes, drug-delivery catheters, sustained release matrixes, electrical sensors, chemical sensors or combinations of any of these at specific locations. These locations will be discussed in detail below.

In one aspect of the invention, therefore, the proximal end of the probe is coupled to an electrical signal source, drug delivery pump, or both which, in turn, is operated to stimulate the predetermined treatment site in the brain structures such as pre-frontal cortex, orbitofrontal cortex, anterior limb of the internal capsule, Nucleus Accumbens, ventral striatum, the ventral Pallidum anterior nucleus of the thalamus, dorsomedial nucleus of the thalamus, intralaminar thalamic nuclei, the cingulate cortex, Amygdala, Hippocampus, Mamillary bodies , the lateral hypothlamnus the Locus Ceruleus, the Dorsal Raphe Nucleus, ventral tegmentum, the Substantia Nigra Pars Compacta and reticulata such that the clinical effects of the psychiatric disorder are reduced.

In particular, the pre-frontal cortex, orbitofrontal cortex, anterior limb of the internal capsule, Nucleus Accumbens, ventral striatum, the ventral Pallidum anterior nucleus of the thalamus, dorsomedial nucleus of the thalamus, intralaminar thalamic nuclei, the cingulate cortex, Amygdala, Hippocampus, Mamillary bodies, the lateral hypothalamus the Locus Ceruleus, the Dorsal Raphe Nucleus, ventral tegmentum, the Substantia Nigra Pars Compacta and reticulata are herein identified by their known anatomical connections and functional brain imaging as being actively involved in channeling or gating the pathological electrical and/or metabolic activity associated with psychiatric disorders. It is important to note that these regions and functions, and its connections are common structural features of human brains, and therefore is a common target across a large number of patients.

In another aspect, the present invention comprises a method of determining the proper therapeutic treatment, e.g., the proper position or placement of the electrodes, for a specific psychiatric disorder comprising the steps of identifying a large sampling of patients, each exhibiting a common specific psychological disorder and then identifying which common region or nuclei exhibits pathological electrical activity during manifestations of the specific disorder. The common regions demonstrating this pathological activity constitute the predetermined treatment site, wherefore a suitable means for affecting the activity of said predetermined treatment site might be employed to ameliorate the psychiatric disorder generically with a high probability of success.

Additionally, however, the instruments utilized in guiding the surgeon in placing the actual electrodes into these structures have a similar degree of variability, or limit of resolution. Fortunately, the state of the art in surgical intervention and the resilience of the brain tissue permits a small degree of manipulation of the electrode once it is inserted. In fact, a number of advanced electrode designs have been presented which permit the micromanipulation of each of the electrical contacts' position without macromanipulation of the overall electrode.

Surgical intervention comprises the second stage of the treatment. Standard neurosurgical techniques for implantation of a probe may be utilized. It shall be understood that the implantation of electrodes, catheters, sensors or any combination both into various implicated structures of the brain (pre-frontal cortex, orbitofrontal cortex, anterior limb of the internal capsule, Nucleus Accumbens, ventral striatum, the ventral Pallidum anterior nucleus of the thalamus, dorsomedial nucleus of the thalamus, intralaminar thalamic nuclei, the cingulate cortex, Amygdala, Hippocampus, Mamillary bodies, the lateral hypothlamus the Locus Ceruleus, the Dorsal Raphe Nucleus, ventral tegmentum, the Substantia Nigra Pars Compacta and reticulata) is within the skill of one ordinarily skilled in the art. It is the application of this technique for the treatment of disorders generally and psychiatric disorders specifically being addressed herein. This technique, therefore, is as follows.

Patients who are to have a probe implanted into the brain, first have a stereotactic head frame, such as the Leksell, CRW, or Compass, mounted to the patient's skull by fixed screws. Subsequent to the mounting of the frame, the patient undergoes a series of magnetic resonance imaging sessions, during which a series of two dimensional slice images of the patient's brain are built up into a quasi-three dimensional map in virtual space. This map is then correlated to the three dimensional stereotactic frame of reference in the real surgical field. In order to align these two coordinate frames, both the instruments and the patient must be situated in correspondence to the virtual map. The head frame is therefore rigidly mounted to the surgical table. Subsequently, a series of reference points are established relative aspects of the frame and patient's skull, so that the computer can adjust and calculate the correlation between the real world of the patient's head and the virtual space model of the patient MRI scans. The surgeon is able to target any region within the stereotactic space of the brain with precision (e.g. within 1 mm). Initial anatomical target localization is achieved either directly using the MRI images, or indirectly using interactive anatomical atlas programs that map the atlas image onto the stereotactic image of the brain. The various anatomical targets in stereotactic X, Y, and Z coordinates are listed in the tables in FIGS. 5 and 6.

The surgery itself can be performed under either local or general anesthetic. An initial incision is made in the scalp, preferably 2.5 centimeters lateral to the midline of the skull, anterior to the coronal suture. A burr hole is then drilled in the skull itself; the size of the hole being suitable to permit surgical manipulation and implantation of the electrode. This size of the hole is generally about 14 millimeters. The dura is then opened, and fibrin glue is applied to minimize cerebral spinal fluid leaks and the entry of air into the cranial cavity. A guide tube cannula with a blunt tip is then inserted into the brain parechyma to a point approximately one centimeter from the target tissue. At this time physiological localization starts with the ultimate aim of correlating the anatomical and physiological findings to establish the final stereotactic target structure.

Physiological localization using single-cell microelectrode recording is preferable for definitive target determination. Sole reliance on anatomical localization can be problematic because of the possible discrepancies between the expected location (expected from the visualization provided by the virtual imaging of the MRI) and the actual position within the skull. Microelectrode recording provides exquisite physiological identification of neuronal firing patterns via direct measures of individual single unit neuronal activity. Single-cell microelectrode recordings obtained from intralaminar thalamic cells typically have a characteristic bursting activity. In addition to microelectrode recording, microstimulation and or macrostimulation may be performed to provide further physiological localization.

Once the final target nucleus has been identified in the real spatial frame of reference, the probe is implanted. General principles guiding the final implantation of a probe involve the placement of the probe in a region, and in an orientation, allowing for maximal efficacy while minimizing the undesired side effects. The currently used brain stimulating electrodes are preferably quadripolar electrodes. The electrode itself is generally approximately 1–1.5 millimeter diameter flexible elastomeric sheath that contains four wound wire leads. The leads terminate at the distal and proximal ends of the sheath in four electrically insulated cylindrical contact pad. The contact pads at the distal end are less than 2 millimeters in length and are separated by an insulating distance, for example between 0.5 and 2 millimeters. At the proximal end, which is anywhere from 25 to 50 centimeters distance from the distal end, a corresponding series of contacts are provided so that the electrode may be coupled to a potential source, or to a coupling lead which permits remote disposition of the signal source.

When used, the drug delivery catheter is generally a silastic tube similar to the one used in the intrathecal drug delivery systems commonly in use. With regard to catheter placement, care is taken not to place the catheter directly within a vascular structure. This can be achieved by combining data from conventional and/or magnetic resonance angiography into the stereotactic targeting model. The distal portion of the catheter has multiple orifices to maximize delivery of the agent while minimizing mechanical occlusion. The proximal portion of the catheter can be connected directly to a pump or via a metal, plastic, or other hollow connector, to an extending catheter.

When used, the sustained release matrix may be utilized independently to deliver a controlled amount of a pharmaceutical or other agent to the specific area of the brain or the intralaminar nuclei of the brain. The sustained release matrix design for stents may be used as an example of a means to deliver a drug at the site of contact, as disclosed for example in U.S. Pat. No. 5,102,417 (Palmaz), in International Patent Application Nos. WO 91/12779 (Medtronic, Inc.), and in WO 90/13332 (Cedars-Sanai Medical Center), which are all hereby incorporated in their entirety by be reference thereto. The sustained release matrix may be used in combination with a lead/electrode to provide electrical stimulation and chemical stimulation. In this scenario, as discussed in more detail in U.S. Pat. No. 6,256,542 which is hereby incorporated in its entirety by reference thereto, the distal end of the assembly is the distal or tip electrode which is provided with an elongated proximally extending shank around which the tine sleeve is mounted. The shank portion of the electrode contains a proximal facing bore in which a monolithic controlled release device is located, containing an agent or drug compounded into a plastic matrix, for example as disclosed in U.S. Pat. No. 4,972,848 issued to DiDomenico or U.S. Pat. No. 4,506,680 issued to Stokes, both incorporated herein by reference in their entireties.

The initial application of the electrical signal through the electrode is then attempted. The electrical signal source is activated thereby applying an oscillating electrical signal, having a specified pulse width. The oscillating electrical signal may be applied continuously or intermittently. One can adjust the stimulating poles, the pulse width, the amplitude, as well as the frequency of stimulation to achieve a desired goal. The application of the oscillating electrical signal may stimulate/increase or block/decrease the neuronal and axonal activity. The frequency of this oscillating electrical signal is then adjusted until the physiological disorder being treated has been demonstrably alleviated. This is then considered the ideal frequency. Once the ideal frequency has been determined, the oscillating electrical signal is maintained at this ideal frequency. Preferably, the oscillating electrical signal is operated at a voltage between about 0.1 $\mu$V to about 20 V. More preferably, the oscillating electrical signal is operated at a voltage between about 0.1 V to about 20 V. Preferably, the electric signal source is operated at a frequency range between about 2 Hz to about 2500 Hz. More preferably, the electric signal source is operated at a frequency range between about 2 Hz to about 200 Hz. Preferably, the pulse width of the oscillating electrical signal is between about 10 microseconds to about 1,000 microseconds. More preferably, the pulse width of the oscillating electrical signal is between about 50 microseconds to about 500 microseconds. Preferably, the application of the oscillating electrical signal is: monopolar when the electrode is monopolar, bipolar when the electrode is bipolar, and multipolar when the electrode is multipolar. Preferably the electrode is an implantable multipolar electrode with either an implantable pulse generator that can be under patient control or a radio frequency controlled device operated by an external transmitter.

The OFC is illustrative of the benefits of the present invention. The OFC has direct and reciprocal excitatory connections, presumably mediated by the neurotransmitter glutamate, with the dorsomedial and anterior thalamic nuclei. In addition, a more indirect loop exists between the OFC, the dorsomedial thalamic nucleus, the ventromedial striatum, and the globus pallidus. Multiple connections also exist between the OFC and the limbic system. The limbic system is a group of structures in the brain, which are thought to mediate the emotional state. At the core of this system is the Papez circuitwhich includes the cingulate gyrus, the anterior thalamic nucleus, the amygdala, the fornix, and the mamillary bodies. The OFC has numerous connections with the Papez circuit via the baslolateral amygdala, the anterior thalmic nucleus and the anterior cingulate gyrus.

There are two coordinated loops passing through the basal ganglia to the thalamus. One, a "motor" loop centered on the sensorimotor, caudate/putamen, globus pallidus, thalamus, and premotor areas. The second "associative" loop involves cortical association areas, caudate/ putamen, globus pallidus, subthalamic nucleus and substantia nigra. Based on this framework, the modern neurosurgical intervention in Parkinson's disease (PD) has been developed While movement disorders, chronic pain, and psychiatric disease might seem as dissimilar entities on the surface, they share common neural substrates. From the earliest observations of OCD, the central role of neuronal areas subserving motor function in its pathogenesis has been speculated. Indeed, Freud himself proposed that the neurologic substrate for the OCD patient's ego lies "at the motor end of the psychical system." Tourette's Disorder, a disease characterized by motor tics as well as OCD-like symptoms demonstrates the phenomenon of a neural substrate capable of producing motor as well as psychiatric disease states. Studies demonstrating the strong clinical and genetic association between Gilles de la Tourette syndrome and OCD have suggested the central role of the basal ganglia in the genesis of OCD symptoms. A similar basal ganglia circuit to the one implicated in Parkinson's Disease has been proposed to explain the production of both motor and obsessional symptoms in Tourette's Disorder. Further analysis of the clinical spectrum of Parkinson's disease has revealed many striking similarities between the "motor" disease of PD and the psychiatric diseases of OCD and Affective Disorder.

Based on these observations, coupled with the serotonergic hypothesis of OCD pathogenesis, a neuronal architecture for the basis of OCD has been proposed. This model hypothesizes that the primary pathogenic mechanism lies in a dysregulation of the basal ganglia/limbic striatal circuits that modulate neuronal activity in and between posterior portions of the orbitofrontal cortex and the medial, especially dorsomedial, thalamic nuclei There are several components to this neuronal model of OCD. The first component involves a reciprocal positive-feedback loop involving the orbitofrontal cortex and the dorsomedial thalamic nucleus, by way of the anterior limb of the internal capsule. The corticothalamic projection is excitatory and mediated primarily by glutamate and aspartate. Although the reciprocal thalamocortical projection's neurotransmitter remains to be identified, multiple studies suggest it to be excitatory as well.

The second component of the OCD model involves the orbitofrontal cortex, the ventral striatum, the ventral pallidum, and the dorsomedial nucleus. While the transmissions of the ventral striatum to the ventral pallidum involve multiple neurotransmitters including Gamma aminobutyric acid (GABA) and substance P, the output of this pathway by way of the ventral pallidum to the thalamus is almost exclusively inhibitory, mediated by GABA. This component is thought to serve as a modulator for the excitatory positive-feedback orbitofrontal thalamic loop described earlier. Another vital aspect of this second component of the OCD model involves serotonergic projections from the dorsal raphe nuclei of the midbrain to the ventral striatum. These are speculated to be inhibitory in nature.

The dorsomedial nucleus also has connections to the limbic system. The limbic system is a group of structures in the brain, which are thought to mediate the emotional state. At the core of this system is the Papez circuit, which includes the cingulate gyrus, the anterior thalamic nucleus, the amygdala, the fornix, and the mamillary bodies. The dorsomedial thalamic nucleus has been shown to have connections with the basolateral amygdala.

The third component of this model involves the limbic system and the circuit of Papez. At its core, OCD is an anxiety disorder, and the impact of the patient's various obsessions/compulsions on his/her emotional state is the hallmark of the disease. Papez concluded that participation from the cerebral cortex is essential for the subjective emotional experience and that emotional expression is dependent on the integrative action of the hypothalamus. Papez devised a circuit based on his observations on neuroanatomic connections to integrate these two structures. The pathway begins from the hippocampal formation to the mammillary body via the fornix. The projection, via the mammillothalamic tract, continues on to the anterior thalamic nuclei. From here, there are widespread connections to the cingulate gyrus. In the aforementioned OCD model, there are numerous connections to the Papez circuit via the DM nuclei and the OFC. These connections could subserve the anxiety/emotional component of OCD.

By synthesizing these three components, OCD symptoms could occur when an aberrant positive-feedback loop develops in the reciprocally excitatory frontothalamic neuronal pathway that is inadequately inhibited/modulated by striatopallidothalamic activity. OCD symptoms would thus be expected to appear when striatopallidothalamic activity is abnormally decreased or when orbitofrontothalamic activity is abnormally increased. Conversely, either increasing the modulating loop or decreasing the excitatory loop would be expected to result in a concomitant decrease in OCD symptom expression. Additionally, modulation of the Papez circuit, may in turn, remove some of the disturbing affect the obsessions or compulsions have on a patient's emotional state. This mechanism is analogous to the model of Parkinson's Disease in which dysregulation in the corpus striatum, secondary to loss of dopaminergic transmission from the Substantia Nigra Pars Compacta (SNc), results in the increase in tonic inhibition of the VL and VA thalamic nuclei by the internal segment of the globus pallidus (Gpi).

Recent functional imaging studies have consistently found evidence that corroborate this model of OCD pathogenesis. Increases in activation correlating with OCD symptoms have been shown to occur in OFC, caudate, thalamus and cingulate areas. After treatment with appropriate medications, including selective serotonin reuptake inhibitors (SSRI), and behavioral therapies, these areas of abnormally increased metabolism were shown to decrease by PET and fMRI studies. Such areas of activation and responses to treatment might prove useful in assessing future neurosurgical treatments for OCD.

The basal ganglia dysregulation has also been implicated in the pathoneurophysiology of Affective Disorders, including Major Depression and Bipolar Disorder. Much of the work implicating the basal ganglia and other structures in the pathogenesis of Affective Disorders comes from imaging studies using PET and fMRI. Abnormalities in metabolism have been demonstrated in the OFC, cingulate, basal ganglia, and amygdala.

In order to examine Affective Disorder from a neurophysiological point of view, emotion can be divided into three components: an expressive component (affect), an internal/representative component (mood), and a modulatory component. The expressive component of emotion, known as affect, represents the external manifestation of a person's internal emotional state. This can further subdivided into two subcomponents: endocrine/humoral and skeletomotor. Connections between the corticomedial amygdala and the hypothalamus via the stria terminalis regulate the release of cortisol and epinephrine in relation to emotional stimuli. Basolateral amygdala connections with the basal ganglia directly influence skeletomotor motivation and behaviors in response to emotional stimuli.

The structures subserving the internal representation of an emotional state, known as mood, remains obscure. Experimental experience however, implicates the amygdala in conjunction with frontal/cingulate cortices, basal ganglia, and hippocampus. Certainly, the Papez circuit also contributes to this internal representation of emotional state. The third component represents a modulatory component between the expressive and internal emotional states. Medial orbitofrontal cortex, cingulate cortex and the basolateral amygdala have all been heavily implicated in this role. These three components can be condensed into a dual circuit model analogous to the one proposed for OCD. One, a limbic-thalamic-cortical loop consisting of the basolateral amygdala, the dorsomedial thalamic nucleus, and the medial and ventrolateral frontal cortices runs in parallel with a limbic-striatal-pallidal-thalamic circuit, consisting of the ventral striatum, the ventral pallidum, and the thalamus. It is possible that Affective Disorder symptoms could be the result of an imbalance in the activity between both of these circuits. Given the numerous connections between these two proposed circuits and the limbic system, the Papez circuit must work in conjunction with these to fully express the symptoms of Affective Disorder.

Various stimulation parameters are tested to assess side effects (such as motor contraction, paresthesias, visual disturbance, pain, and autonomic modulation) or clinical efficacy. The electrical stimulation can be applied to the patient's entire nuclei (pre-frontal cortex, orbitofrontal cortex, anterior limb of the internal capsule, Nucleus Accumbens, ventral striatum, the ventral Pallidum anterior nucleus of the thalamus, dorsomedial nucleus of the thalamus, intralaminar thalamic nuclei, the cingulate cortex, Amygdala, Hippocampus, Mamillary bodies, the lateral hypothlamus the Locus Ceruleus, the Dorsal Raphe Nucleus, ventral tegmentum, the Substantia Nigra Pars Compacta and reticulata) or subsections such as to one or more portions of the patient's intralaminar nuclei. In addition to being applied to the patient's intralaminar nuclei or portion thereof, the electrical stimulation can also extend to other regions of the brain. Preferably, the electrical stimulation is applied only to the patient's intralaminar nuclei or portion thereof without stimulating other regions of the patient's brain. For example, the electrical stimulation can be applied to all portions of the patient's intralaminar nuclei except the centromedian-parafasicularis, except the central lateral, or except both the central lateral and centromedian-parafasicularis. Electrical stimulation can be epidural in case of prefrontal cortex and orbitofrontal cortex, or can be subdural or intraparenchymal.

The architecture of the brain provides a substantial advantage in the search for a general solution to undesirable neuronal activity. This design advantage takes the form of a centralized signaling nexus through which many of the brain's disparate functions are channeled in an organized and predictable manner. More particularly, the thalamus is comprised of a large plurality (as many as one hundred or more) of neuronal bundles or nuclei, as well as white matter tracts (highways of information) which receive and channel nerve activity from all areas of the nervous system and interconnects various activities within the brain. The thalamus is analogous to a centralized train station such as a grand central station. Many different train tracks come together, and many trains carrying many different cargoes enter and exit; however, if one has a schedule and a map, it is easy to find all the trains that carry coal because all coal carriers are routed through the same tracks.

In other words, in the thalamus, all the brain signals travel in an organized fashion. The activity in the peripheral areas of the brain which are associated with the same, or similar conditions, are channeled through the same areas of the thalamus. In this way, the thalamus acts as a train relay station, or as a post office, re-routing disparate signals along similar paths when the appropriate outcomes of the original signals are similar.

It is this observation that would appear to permit the treatment of common neurological disorders, particularly psychiatric disorders, by brain stimulation of one specific area, rather than having to customize the (gross) placement of the stimulator and/or catheter for each patient. For every one ascending connection from the thalamus to the cortex, there are 40 descending connections from the cortex to the thalamus. Thus, any abnormality in the cortex from various diseases can be manifested in the thalamus and thus the thalamic nuclei may be used for intervention.

Figure 3:
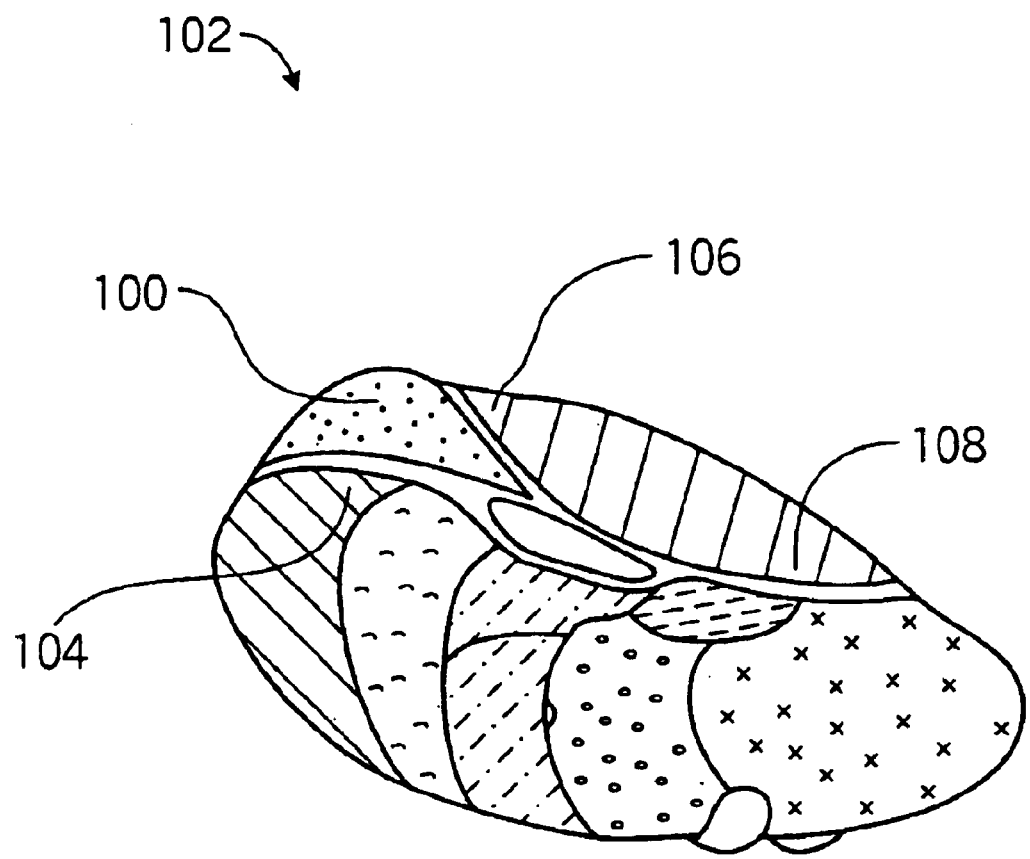
FIG. 3 illustrates the layout and orientation of the intralaminar nuclei ("ILN") including the position of the related subdivisions and nuclei with respect to the thalamus.
Figure 4:
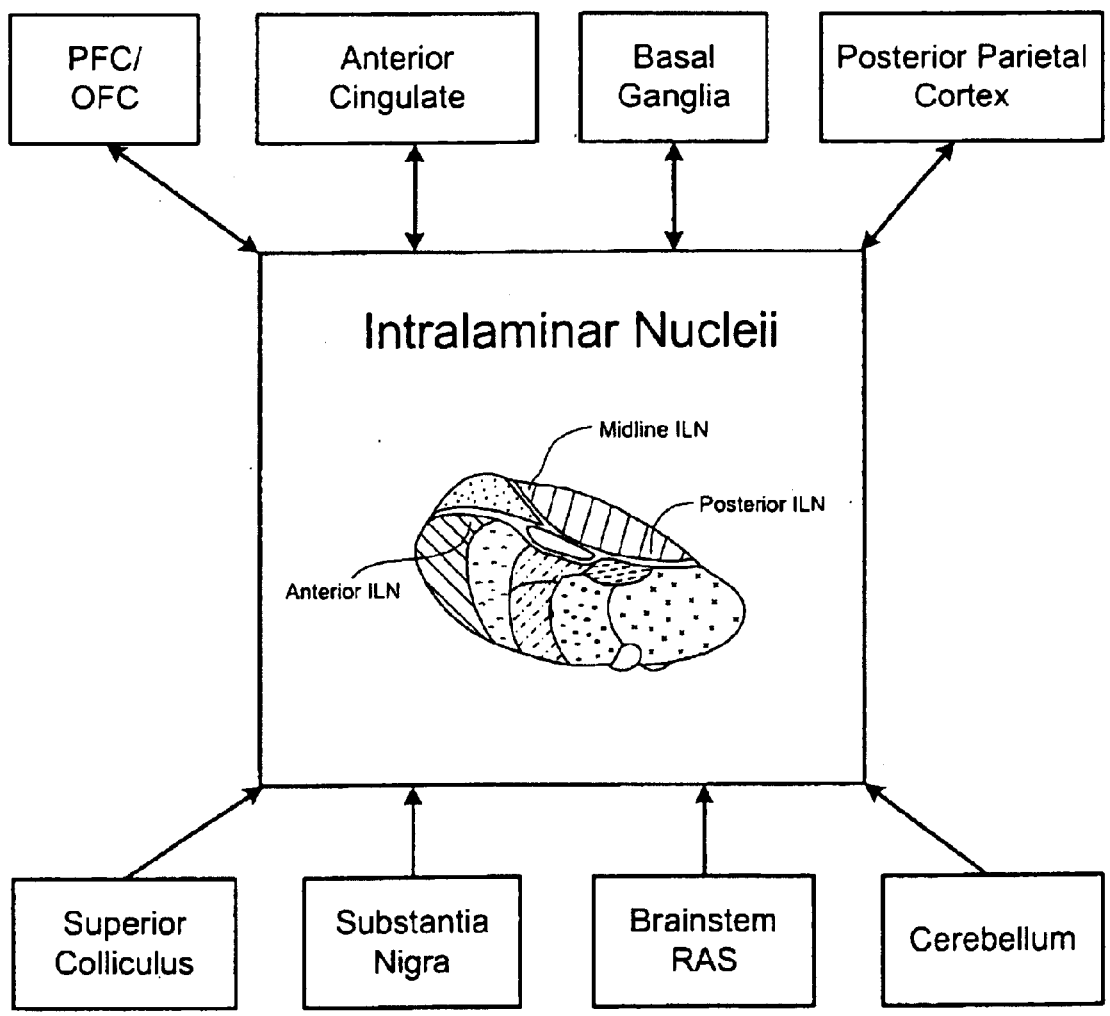
FIG. 4 illustrates the ILN nuclei and their interconnections to the various structures involved in the psychiatric circuitry.

As is shown in FIGS. 1, 3, and 4, the anterior thalamic nuclei are coupled most directly to the frontal lobes and the dorsomedial thalamic nucleus is coupled most directly to the orbitofrontal cerebral cortex which is most associated with personality and behavior. The orbital frontal cortex (OFC) is particularly implicated in the pathogenesis of various psychiatric diseases. There are two main loops connecting the dorsomedial nucleus and the OFC. A direct, reciprocally excitatory loop is mediated by the neurotransmitter glutamate. An indirect, modulatory loop occurs via connections through the ventromedial striatum and globus pallidus, and is thought to be mediated by multiple neurotransmitters including GABA, dopamine, and serotonin.

Referring more particularly to FIG. 1 the orbitofrontal cerebral cortex (201) consists of a subsection of the frontal cerebral cortex (203), the most anterior portion of the brain. Specifically, the orbitofrontal cortex lies medially to the inferior frontal gyrus and lateral to the gyrus rectus. The orbitofrontal cortex (OFC) is also distinct cytotechtonically, according to the widely accepted classification scheme of Brodmann. The anatomic connections of the OFC with dorsomedial and anterior thalamic nuclei, the striatum, the pallidum, and the Papez circuit (which is thought to mediate emotional affect in man) are illustrated in a conceptual map provided as FIG. 4. These circuits are all interconnected to each other as well as to the thalamus (anterior nucleus, dorsomedial nucleus, intralaminar nuclei), the basal ganglia and the limbic system (amygdala, hippocampus, cingulate gyrus).

The thalamus, which is a central integrating structure also contains the intralaminar nuclei. The ILN is schematically illustrated in FIG. 3 and the XYZ coordinates are provided in the table shown in FIG. 6. The ILN have diff-use projections to the various structures implicated in psychiatric activity/disorders as is illustrated for example in FIG. 2. In looking at other aspects of the neural circuitry underlying psychiatric disorders, reference is made to FIG. 3. As shown in FIG. 3, within the intralaminar nuclei 102 are principally the anterior 104, midline 106, and posterior 108 subgroups. The anterior subgroups 104 include the central lateral (CL) and paracentralis regions. The posterior subgroups 108 include the centromedian-parafascicularis complex (Cm-Pf). The midline 106 and other related subgroups include the centre medial (CM) nuclei and paraventricularis (Pv).

FIG. 6 shows the ILN subdivisions and their projection targets as well as the stereotactic X (Medial-lateral), Y (anterior-posterior) and Z (superior-inferior) coordinates of these structures. Accordingly, based on the table in FIG. 6, as an example, it can be deduced that stimulation of the anterior subdivision 104 and more specifically, the paracentralis nuclei can influence the abnormal activity in the orbitofrontal cortex manifesting in anxiety disorders such as OCD. Similarly, it can be deduced that stimulation of the midline ILN 106 can affect the limbic circuit and thus influence abnormal activity in mood disorders such as major depression. This is but a few examples of the utility of the present invention using the ability to modulate ILN to affect the various disruptions in the projected regions of the brain.

FIG. 2 shows the ILN nuclei and their interconnections to the various structures involved in the psychiatric circuitry. The intralaminar nuclei have important anatomical and physioloigcal connections that involve the circuitry of psychiatric disorders. Intralaminar nuclei are a small set of nuclei located in the paramedian thalamus. The intralaminar nuclei can be divided into an anterior group and a posterior group. FIG. 3 illustrates the anatomical connections of the intralaminar nuclei ("ILN") with distributed circuits underlying arousal, attention, intention, emotions, working memory, and gaze and motor control. The anterior ILN group projects widely throughout the neocortex to primary sensory and motor areas and association cortices, while the posterior group projects mainly to sensory-motor and premotor areas and striatal targets. The anterior ILN group includes the central lateral nucleus ("CL"), which projects to the frontal eye field ("FEF"), motor cortex, and, more heavily, to the posterior parietal cortex ("PPC"). The paracentralis ("Pc") nucleus projects to the prefrontal cortex (with heavier projection than CL) and very strongly to the inferior parietal lobe and visual association cortices. The central medial ("CeM") nucleus, which also projects to the prefrontal and visual association cortices, also projects to the cingulate cortex and pregenual areas and to the medial cortical surface and orbitofrontal cortex. Included within the meaning of intralaminar nuclei, as used herein, is the Paraventricular nucleus ("Pv"), which is strongly associated with the limbic system, and midline thalamic nuclei. Projections to prefrontal cortex ("IPFC") and anterior cingulate cortex arise, as well, from the anterior intralaminar group. The CL is also known to project to the primary visual cortex in the cat and monkey. The posterior ILN group is dominated by the centromedian-parafasicularis complex ("Cm-Pf"), which strongly projects to areas 6 and 4. In primates, the CmPf undergoes a notable expansion, and the CL also expands and develops further subdivisions. This system projects strongly to the caudate (from Pf), putamen (from Cm nuclei of the basal ganglia), and prefrontal and parietal association cortices. A small projection (Pf) also goes to the FEF. The intralaminar nuclei projections to the striatum per se are considered the principle efferent connections of the intralaminar nuclei and include anterior group projections to the caudate, as well. While not wishing to be bound by theory, it would appear then that the intralaminar nuclei (including the midline nuclei) is in a preferred position to modulate the large thalamo-cortical-basal ganglia loops, especially to synchronize their function.

Referring more particularly to FIG. 3, the anterior thalamic nuclei 100 are located in the most anterior portion of the thalamus and are interconnected with the frontal lobes. The intralaminar nuclei 102 are located in the paramedian thalamus (dividing each of the lobes of the thalamus along a Y shaped vertical planar geometry which cuts through the posterior to anterior axis of each lobe). The intralaminar nuclei 102 have more diffuse projections. Together these nuclei groups are the most likely associated with psychological disorders. Referring now to FIG. 3, within the intralaminar nuclei 102 are principally the anterior 104, midline 106, and posterior 108 subgroups. The anterior subgroups 104 include the central lateral (CL) and paracentralis regions. The posterior subgroups 108 include the centromedian-parafascicularis complex (Cm-Pf). The midline 106 and other related subgroups include the centre medial (CeM) nuclei and paraventricularis (Pv).

The anterior thalamic nuclei are coupled most directly to the frontal lobes or Orbital Frontal Cortex ("OFC") which are most associated with personality and behavior. The posterior subgroup of the intralaminar nuclei, including the centromedian-parafascicularis, is coupled most directly to the prefrontal, permotor, and parietal cortices. The anterior subgroup, including the central lateral and paracentralis nuclei, is most directly connected to the parietal, visual association, prefrontal, frontal, and superior temporal cortices as well as the frontal eye field. The midline and related intralaminar subgroups, including the paraventricularis, centre medial, midline nuclei, are connected to the orbital frontal cortex, the hippocampus, the limbic cortex, and the amygdala.

The intralaminar nuclei receive ascending inputs from several components of the ascending reticular arousal system, including the pedunculopontine cholinergic group (lateral dorsal tegmentum), mesencephalic reticular formation, locus ceruleus, and dorsal raphe. Thus, the intralaminar nuclei are targets of modulation by a wide variety of neurotransmitter agents, including acetylcholine (pedunculopontine, lateral dorsal tegmentum, and mesencephalic reticular formation neurons), noradrenaline (locus ceruleus) serotonin (raphe nuclei), and histamine (hypothalamus). Also received by the intralaminar nuclei are nociceptive, cerebellar, tectal, pretectal, and rhinencephalic inputs. Descending inputs reciprocally relate components of the intralaminar nuclei with their cortical projections.

Although each cell group within the intralaminar nuclei projects to many separate cortical targets, each neuron of the intralaminar nuclei has a narrowly elaborated projection and receives its cortical feedback from the same restricted area. The reciprocal projections between the intralaminar nuclei and cortex have a distinctive laminar pattern that differs from the more well-known pattern of the reciprocal projections of the relay nuclei. The intralaminar nuclei neurons synapse in Layer I on the terminal dendritic tufts of layers III and V pyramidal cells and in layers V and VI, whereas neurons of the relay nuclei terminate primarily in cortical layers III and IV. Feedback to intralaminar nuclei neurons originates in Layer V, but feedback to the relay nuclei originates in Layer VI. In the cat, the dominant corticothalamic input to the CL originates in the PFC, whereas the visual areas, including area 17, also project directly to the CL.

As used herein, intralaminar nuclei also include paralamellar regions, such as parts of the medial dorsal ("MD") nucleus and the midline nuclei (which are sometimes distinguished from the intralaminar nuclei but, for purposes of the present application, are not). The exact location of the thalamic nuclei and their corresponding cortical connections can be determined via stereotactic techniques. Stereotactic techniques are routinely used to triangulate and precisely locate structures which are identified via specific coordinates, usually determined with respect to two standard centralized brain landmarks called the anterior commisure (AC) and the posterior commissure (PC). This is analogous to a global positioning system that can determine the precise location of individuals.

The intralaminar nuclei in particular project to all the components of the psychiatric circuits described above. Thus, stimulation of the intralaminar nuclei (either all or any or combination) can affect the specific components of the structures involved in the psychiatric circuitry described above. Although one aspect of the present invention is to stimulate a pre-determined area of the brain to impact the psychiatric disorder described above (e.g. OCD or Anxiety disorder), a preferred embodiment of the present invention is to stimulate a pre-determined area or areas of the ILN to have affect the connected region of the brain. A further aspect of this embodiment may be the detection via sensors in one portion of the brain and stimulation in the ILN to affect or impact the portion of the brain so indicated. As an example, if an OCD event is detected in the orbital frontal cortex, stimulation may occur in the area of the ILN associated with the orbital frontal cortex The method of the present invention can further comprise selecting one or more subdivisions of the patient's intralaminar nuclei for stimulation. In particular, the subdivision to be stimulated can be one that modulates the specific function that is impaired in the patient.

As indicated above, stimulation can be applied to an entire region, to a group of nuclei or to one, two, or more specific subdivisions thereof. Stimulation can be applied to the one, two, or more specific subdivisions in either or both brain hemispheres. In some cases, it can be advantageous to apply electrical stimulation to two or more subdivisions of the intralaminar nuclei that modulate separate cortical regions. Stimulation may be electrical, chemical, or both. As used herein, cortical regions are considered to be separate when they are not contiguous on the cortical mantle or they are considered separate in function based on known anatomical or physiological characteristics of cells within their borders. For example, the patient's central medial and centromedian-parafasicularis intralaminar nuclei subdivisions, which respectively project strongly to the orbitofrontal and premotor regions of the cortex, can be stimulated.

Where two or more subdivisions of the intralaminar nuclei are stimulated, both can lie in the same thalamus. Alternatively, at least one of the two or more subdivisions of the intralaminar nuclei can lie in the left thalamus while at least one of the two or more subdivisions of the intralaminar nuclei lies in the right thalamus. Preferably, at least one of the two or more subdivisions and, more preferably, at least two of the two or more subdivisions of the intralaminar nuclei to which electrical stimulation is applied modulates the specific cognitive function which is impaired in the patient.

With regard to a chemical based system, the drug-delivery pump may be programmed with an initial nominal dose scheme. Examples of suitable pharmaceutical agents that can be used in conjunction with the electrical stimulation methods of the present invention include known excitatory and inhibitory transmitters that influence intralaminar nuclei function. Excitatory transmitters would preferably include acetylcholine ("Ach"), noradrenaline ("NE"), and/or serotonin ("5-HT") or analogues thereof. Inhibitory transmitters would include primary gamma-aminobutyric acid ("GABA") or analogs thereof. Other amino acid transmitters know to affect the intralaminar nuclei, such as adenosine or glutamate, can also be used.

Psychiatric disorders treated by electrical stimulation and/or pharmacotherapy, however, may take up to six months to demonstrate clinical efficacy. Long term adjustment of the signal or dosage being applied by the power source or drug-delivery pump may be required to optimize the outcome. If the patient's symptoms do not subside, the surgeon will attempt to adjust all of the parameters until they do.

Typically, the proximal end of the probe, is connected to remotely located signal source generator, subcutaneous drug pump or sensor processor (hereafter referred to generally as "remote device") disposed within the patient's body. A specially designed plastic cap is generally provided to seat in the burr hole, and permit the proximal end of the probe to pass out through the skull. The incision in the patient's skull is then sutured closed with the probe temporarily stored under the skin. If the patient is not already under general anesthesia, the patient is so disposed and a tunnel is formed under the dermal layers, connecting the incision in the scalp to the remote location, usually the infraclavicular region, beneath the collar bone—where cardiovascular pace makers are implanted. Subsequently, the probe is joined to a coupling extending from the remote device. Generally, the manner in which the probe and the remote device are coupled utilizes the same terminal contacts as would be used for direct coupling to the power source.

Once the surgery is complete, a non-contrast CT scan is taken to ensure that there is no intracranial hematoma. Subsequently, various stimulation parameters are programmed and patients are assessed for any side effects as well as clinical efficacy. As behavioral and related cognitive improvement may not occur immediately, long-term benefits may not be achieved until multiple adjustments are accomplished.

Where two or more subdivisions of the patient's brain (e.g. intralaminar nuclei) are electrically stimulated periodically and at the same frequency, such stimulation can be completely in phase, partially in phase and partially out of phase, or completely out of phase. When such stimulation is substantially entirely in phase, it is said to be synchronized. In a preferred embodiment of the present invention, the electrical stimulation applied to two or more subdivisions of the patient's intralaminar nuclei is synchronized.

While there has been described and illustrated specific embodiments of new and novel methods of treatment for neurological disorders, it will be apparent to those skilled in the art that variations and modifications are possible without deviating from the broad spirit and principle of the present invention which shall be limited solely by the scope of the claims appended hereto.

Having thus set forth the preferred embodiments, the invention is now claimed to be:

1. A method of treating a disorder associated with a specific area in a brain comprising:
   implanting a device in contact with an intralaminar nuclei of the brain;
   sensing activity in the specific area of the brain, wherein the specific area of the brain is different than the intralaminar nuclei, and wherein the specific area of the brain is different than the intralaminar nuclei and the sensing activity occurs at a location distal from the device location; and
   operating the device to modulate the intralaminar nuclei in response to said activity to thereby affect the disorder associated with the specific area of the brain.

2. The method of claim 1, wherein the device is an electrode assembly.

3. The method of claim 1, wherein the activity being sensed is electrical activity.

4. The method of claim 1, wherein the device is sustained-release matrix.

5. The method of claim 1, wherein said specific area is selected from the group consisting of the pre-frontal cortex, orbitofrontal cortex, anterior limb of the internal capsule, Nucleus Accumbens, ventral striatum, the ventral Pallidum anterior nucleus of the thalamus, dorsomedial nucleus of the thalamus, intralaminar thalamic nuclei, the cingulate cortex, Amygdala, Hippocampus, Mamillary bodies, the lateral hypothalamus, the Locus Ceruleus, the Dorsal Raphe Nucleus, ventral tegmentum, the Substantia Nigra Pars Compacta and reticulata.

6. The method of claim 1, wherein said disorder is selected from the group consisting of obsessive compulsive disorder, generalized anxiety disorder, post traumatic stress disorder, panic attacks, social phobia, major depression, bipolar disorder, schizophrenia, and substance abuse disorders/additions.

7. The method of claim 1, wherein said step of sensing occurs epidurally, subdurally, or on the scalp.

8. The method of claim 1, wherein said step of sensing occurs at the local milieu of the electrode.

9. A method of affecting a psychiatric activity in a specific area of the brain comprising:
  placing an electrode in contact with an intralaminar nuclei of the brain; and
  operating the device to provide stimulation to the intralaminar nuclei to thereby affect the psychiatric activity in the specific area of the brain, the specific area of the brain being different than the intralaminar nuclei.

10. The method of claim 9, wherein the stimulation is electrical.

11. The method of claim 10, wherein the device is an electrode assembly.

12. The method of claim 9, wherein the stimulation is chemical.

13. The method of claim 12, wherein the device is a sustained-release matrix.

14. The method of claim 9, wherein said specific area is selected from the group consisting of the pre-frontal cortex, orbitofrontal cortex, anterior limb of the internal capsule. Nucleus Accumbens, ventral striatum, the ventral Pallidum anterior nucleus of the thalamus, dorsomedial nucleus of the thalamus, intralaminar thalamic nuclei, the cingulate cortex, Amygdala, Hippocampus, Mamillary bodies, the lateral hypothalamus, the Locus Ceruleus, the Dorsal Raphe Nucleus, ventral tegmentum, the Substantia Nigra Pars Compacta and reticulate.

15. A method of affecting psychiatric activity in a patient comprising:
  identifying a portion of the patient's ILN intralaminar nuclei which is in communication with a predetermined region of the patient's brain, said predetermined region of said patient's brain being associated with the psychiatric activity;
  and modulating the portion of the patient's ILN to effectuate the psychiatric activity.

16. The method of claim 15, wherein the identification of a portion of the patient's intralaminar nuclei is based upon a composite of other patient's intralaminar nuclei activity.

17. The method of claim 15, wherein the identifying step is independent of an exhibition of a pathologic condition in the predetermined region of said patient's brain.

18. The method of claim 15, wherein the psychiatric activity is selected from the group consisting of happiness, fear, anger, anxiety, euphoria, and sadness.

19. The method of claim 15, wherein the modulation of the portion of the patient's ILN is accomplished using chemical stimulation.

20. A method of treating a disorder associated with specific area in a brain comprising:
  implanting a device wherein the device includes a sustained release matrix in contact with an intralaminar nuclei of the brain;
  sensing activity in the specific area of the brain, wherein the sensing activity occurs at a location distal from the device location; and
  operating the device to modulate the intralaminar nuclei in response to said activity to thereby affect the disorder associated with the specific area of the brain.

21. The method of claim 20, wherein modulation occurs via release of a chemical from the sustained release matrix.

22. The method of claim 20, wherein the specific area of the brain in which the device is implanted is different than the intralaminar nuclei.

23. The method of claim 17, wherein said step of sensing occurs epidurally, subdurally, or on the scalp.

* * * * *

UNITED STATES PATENT AND TRADEMARK OFFICE
CERTIFICATE OF CORRECTION

PATENT NO. : 6,708,064 B2 Page 1 of 1
APPLICATION NO. : 10/036340
DATED : March 16, 2004
INVENTOR(S) : Ali Rezai It is certified that error appears in the above-identified patent and that said Letters Patent is hereby corrected as shown below:

RELATED US APPLICATION DATA

Line 63 – Please delete entire paragraph.

Signed and Sealed this

Sixth Day of February, 2007

JON W. DUDAS
*Director of the United States Patent and Trademark Office*